US008772466B2

(12) United States Patent
Nelson et al.

(10) Patent No.: US 8,772,466 B2
(45) Date of Patent: *Jul. 8, 2014

(54) ZEA MAYS NFB2 PROMOTER

(75) Inventors: Donald E. Nelson, Stonington, CT (US); Brendan S. Hinchey, Mystic, CT (US); Michelle Lacy, St. Louis, MO (US); James A. Morrell, St. Louis, MO (US); Andrey A. Boukharov, Wildwood, MO (US); Zhaolong Li, St. Louis, MO (US); Wei Wu, St. Louis, MO (US); Linda Lutfiyya, St. Louis, MO (US); Maolong Lu, St. Louis, MO (US); David K. Kovalic, Clayton, MO (US); Qi Wang, St. Louis, MO (US); Ping Li, St. Peters, MO (US); Yongwei Cao, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 854 days.

This patent is subject to a terminal disclaimer.

(21) Appl. No.: 12/331,214

(22) Filed: Dec. 9, 2008

(65) Prior Publication Data

US 2009/0137394 A1 May 28, 2009

Related U.S. Application Data

(60) Division of application No. 11/765,504, filed on Jun. 20, 2007, now Pat. No. 7,629,455, which is a continuation-in-part of application No. 11/635,706, filed on Dec. 7, 2006, now Pat. No. 7,491,813.

(60) Provisional application No. 60/748,114, filed on Dec. 7, 2005, provisional application No. 60/816,086, filed on Jun. 23, 2006.

(51) Int. Cl.
| | | |
|---|---|---|
| C12N 15/82 | (2006.01) | |
| A01H 5/00 | (2006.01) | |
| C07H 21/04 | (2006.01) | |

(52) U.S. Cl.
USPC .......... 536/24.1; 435/419; 800/278; 800/295; 800/298; 800/300

(58) Field of Classification Search
None
See application file for complete search history.

(56) References Cited

U.S. PATENT DOCUMENTS

| | | | | |
|---|---|---|---|---|
| 5,294,593 A | * | 3/1994 | Khan | 504/100 |
| 7,629,455 B2 | * | 12/2009 | Nelson et al. | 536/24.1 |
| 2007/0130645 A1 | | 6/2007 | Wu et al. | 536/24.1 |

OTHER PUBLICATIONS

Donald et al. Mutation of either G box or I box sequences profoundly affects expression from the *Arabidopsis* rbcS-1A promoter. (1990), EMBO J. vol. 9; pp. 1717-1726.*
Benfey et al. The cauliflower mosaic virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol. vol. 24; pp. 105-117.*
Whitelaw et al. OGNAA57THZM_0.7_1.5_KB *Zea mays* genomic clone ZMMBMa0324117, genomic survey sequence. (2003) GenBank Accession CC698783; pp. 1-2.*
Rieping et al. Synergistic effect of upstream sequences, CCAAT box elements, and HSE sequences for enhanced expression of chimaeric heat shock genes in transgenic tobacco. (1992) MGG; vol. 231; pp. 226-232.*
Benfey et al., "The CaMV 35S enhancer contains at least two domains which can confer different developmental and tissue-specific expression patterns," *EMBO J.*, 8(8):2195-2202, 1989.
Benfey et al., "The cauliflower mosaic virus 35S promoter: combinatorial regulation of transcription in plants," *Science*, 250:959-966, 1990.
Cho et al., "Regulation of root hair initiation and expansin gene expression in *Arabidopsis*," *The Plant Cell*, 14:3237-3253, 2002.
Donald et al., "Mutation of either G box of I box sequences profoundly affects expression from the *Arabidopsis* rbcS-1A promoter," *EMBO J.*, 9(6):1717-1726, 1990.
GenBank Accession No. BT041097, dated Jul. 30, 2008.
GenBank Accession No. CC698783, dated Jun. 19, 2003.
GenBank Accession No. NM_001112582, dated Dec. 18, 2007.
Kim et al., "A 20 nucleotide upstream element is essential for the nopaline synthase (nos) promoter activity," *Plant Molecular Biology*, 24:105-117, 1994.
Odell et al., "Identification of DNA sequences required for activity of the cauliflower mosaic virus 35S promoter," *Nature*, 313:810-812, 1985.
Piechulla et aL, "Identification of tomato Lhc promoter regions necessary for circadian expression," *Plant Molecular Biology*, 38:655-662, 1998.
Welsch et al., "Structural and functional characterization of the phytoene synthase promoter from *Arabidopsis thaliana*," *Planta*, 216:523-534, 2003.

\* cited by examiner

*Primary Examiner* — Cathy Kingdon Worley
(74) *Attorney, Agent, or Firm* — Dentons US LLP; Carine M. Doyle, Esq.

(57) ABSTRACT

The present invention provides non-coding regulatory element polynucleotide molecules isolated from the transcription factor Nuclear Factor B (NFB2) gene of *Zea mays* and useful for expressing transgenes in plants. The invention further discloses compositions, polynucleotide constructs, transformed host cells, transgenic plants and seeds containing the *Zea mays* NFB2 regulatory polynucleotide sequences, and methods for preparing and using the same.

15 Claims, 1 Drawing Sheet

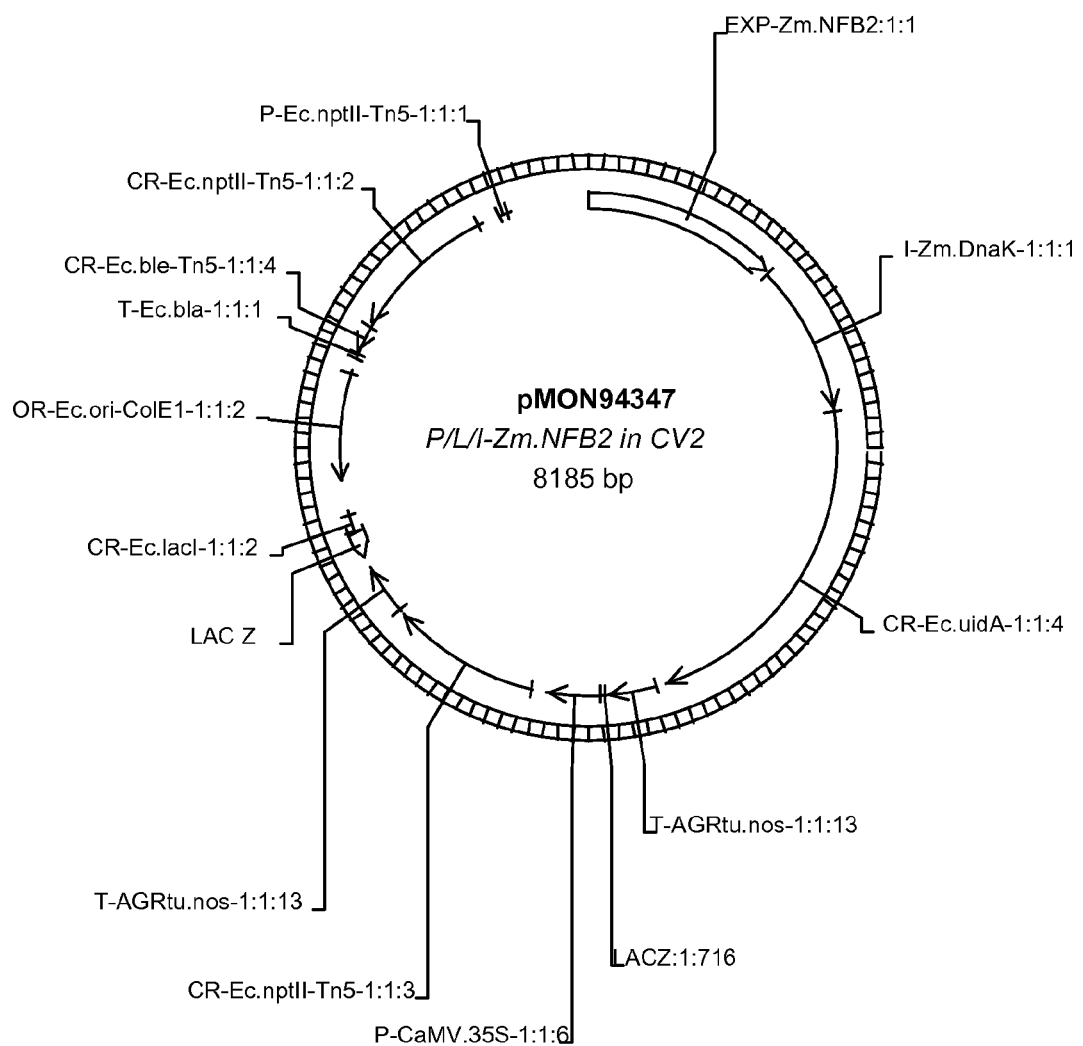

ZEA MAYS NFB2 PROMOTER

This application is a division of U.S. application Ser. No. 11/765,504, filed Jun. 20, 2007 now U.S. Pat. No. 7,629,455, which is a continuation-in-part of U.S. application Ser. No. 11/635,706 filed Dec. 7, 2006 now U.S. Pat. No. 7,491,813, which itself claims benefit under 35USC §119(e) to U.S. Provisional Application Ser. No. 60/748,114 filed Dec. 7, 2005; and additionally claims benefit under 35USC §119(e) United States Provisional Application Ser. No. 60/816,086 filed Jun. 23, 2006, each of the disclosures of which are herein incorporated by reference in their entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa__01305.txt, which is 3,675 bytes (measured in Microsoft Windows®) and was created on Jun. 11, 2007, all of which are incorporated herein by reference.

FIELD OF THE INVENTION

The present invention relates to the field of plant molecular biology and plant genetic engineering, and polynucleotide molecules useful for gene expression in plants. Specifically, the present invention discloses nucleic acid sequences from *Zea mays* (corn) comprising regulatory elements, such as promoters, leaders and introns, identified from the transcription factor Nuclear Factor B (NFB) gene. The invention further discloses constructs, cells and plants comprising said regulatory elements, and methods of producing and using the same.

BACKGROUND

One of the goals of plant genetic engineering is to produce plants with agronomically desirable characteristics or traits. The proper expression of a desirable transgene in a transgenic plant is one way to achieve this goal. Elements having gene regulatory activity, i.e. regulatory elements such as promoters, leaders, introns and transcription termination regions, are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall gene expression. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Corn Actin 1, the promoter from the actin 1 gene of *Oryza sativa* (U.S. Pat. No. 5,641,876); and P—NO: S, the promoter from the nopaline synthase gene of *Agrobacterium tumefaciens* are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants. One example of this is the need for regulatory elements capable of driving gene expression in different types of tissues.

The genetic enhancement of plants and seeds provides significant benefits to society. For example, plants and seeds may be enhanced to have desirable agricultural, biosynthetic, commercial, chemical, insecticidal, industrial, nutritional, or pharmaceutical properties. Despite the availability of many molecular tools, however, the genetic modification of plants and seeds is often constrained by an insufficient or poorly localized expression of the engineered transgene.

Many intracellular processes may impact overall transgene expression, including transcription, translation, protein assembly and folding, methylation, phosphorylation, transport, and proteolysis. Intervention in one or more of these processes can increase the amount of transgene expression in genetically engineered plants and seeds. For example, raising the steady-state level of mRNA in the cytosol often yields an increased accumulation of transgene expression. Many factors may contribute to increasing the steady-state level of an mRNA in the cytosol, including the rate of transcription, promoter strength and other regulatory features of the promoter, efficiency of mRNA processing, and the overall stability of the mRNA.

Among these factors, the promoter plays a central role. Along the promoter, the transcription machinery is assembled and transcription is initiated. This early step is often rate-limiting relative to subsequent stages of protein production. Transcription initiation at the promoter may be regulated in several ways. For example, a promoter may be induced by the presence of a particular compound or external stimuli, express a gene only in a specific tissue, express a gene during a specific stage of development, or constitutively express a gene. Thus, transcription of a transgene may be regulated by operably linking the coding sequence to promoters with different regulatory characteristics. Accordingly, regulatory elements such as promoters, play a pivotal role in enhancing the agronomic, pharmaceutical or nutritional value of crops.

At least two types of information are useful in predicting promoter regions within a genomic DNA sequence. First, promoters may be identified on the basis of their sequence "content," such as transcription factor binding sites and various known promoter motifs. (Stormo, Genome Research 10: 394-397 (2000)). Such signals may be identified by computer programs that identify sites associated with promoters, such as TATA boxes and transcription factor (TF) binding sites. Second, promoters may be identified on the basis of their "location," i.e. their proximity to a known or suspected coding sequence. (Stormo, Genome Research 10: 394-397 (2000)). Promoters are typically contained within a region of DNA extending approximately 150-1500 basepairs in the 5' direction from the start codon of a coding sequence. Thus, promoter regions may be identified by locating the start codon of a coding sequence, and moving beyond the start codon in the 5' direction to locate the promoter region.

It is of immense social, ecological and economic interests to develop plants that have enhanced nutrition, improved resistance to pests, and tolerance to harsh conditions such as drought. Thus, the identification of new genes, regulatory elements (e.g., promoters), etc. that function in various types of plants is useful in developing enhanced varieties of crops. Clearly, there exists a need in the art for new regulatory elements, such as promoters, that are capable of expressing heterologous nucleic acid sequences in important crop species. We found that isolated regulatory elements from the *Arabidopsis thaliana* S-adenosylmethionine synthetase gene, particularly the promoter, leader and intron regulatory elements, provide these enhanced expression patterns for an operably linked transgene in a transgenic plant. Promoters that exhibit both constitutive expression and tissue-specific patterns are of great interest in the development of plants that exhibit agronomically desirable traits.

SUMMARY

The present invention describes the composition and utility for non-coding regulatory element promoter molecules identified from the *Zea mays* (corn) transcription factor Nuclear Factor B gene, also known as the NFB2 gene.

The present invention includes and provides a substantially purified nucleic acid molecule, or a DNA construct useful for modulating gene expression in plant cells, or a transgenic plant cell, or a transgenic plant, or a fertile transgenic plant, or a seed of a fertile transgenic plant, comprising a nucleic acid sequence wherein the nucleic acid sequence: i) hybridizes under stringent conditions with a sequence elected from the group consisting of SEQ ID NO: 1 through SEQ ID NO: 5 or any complements thereof, or any fragments thereof, or any cis elements thereof; or ii) exhibits an 85% or greater identity to a sequence elected from the group consisting of SEQ ID NO: 1 through SEQ ID NO: 5, or any complements thereof, or any fragments thereof, or any cis elements thereof.

The present invention includes and provides a method of transforming a host cell comprising: a) providing a nucleic acid molecule that comprises in the 5' to 3' direction: a nucleic acid sequence that: i) hybridizing under stringent conditions with a sequence selected from the group consisting of SEQ ID NO: 1 through SEQ ID NO: 5, or any complements thereof, or any fragments thereof, or any cis elements thereof, or ii) exhibiting an 85% or greater identity to a sequences elected from the group consisting SEQ ID NO: 1 through SEQ ID NO: 5, or any complements thereof, or any fragments thereof, or any cis elements thereof, operably linked to a transcribable polynucleotide molecule sequence; and b) transforming said plant with the nucleic acid molecule.

In one embodiment, the invention provides regulatory elements isolated from *Zea mays* and useful for modulating gene expression in transgenic plants In another embodiment, the invention provides DNA constructs containing polynucleotide molecules useful for modulating gene expression in plants. In another embodiment, the invention provides transgenic plants and seeds comprising the DNA constructs, comprising a promoter or other regulatory elements operably linked to a heterologous DNA molecule, useful for modulating gene expression in plants. The transgenic plant preferably expresses an agronomically desirable phenotype.

BRIEF DESCRIPTION OF THE DRAWINGS

FIG. 1: Diagrammatic representation of plasmid pMON94347, comprising P-Zm.NFB2-1:1:2, L-Zm.NFB2-1:1:1, I-Zm.NFB2-1:1:1, L-Zm.NFB2-1:1:2.

DETAILED DESCRIPTION OF THE INVENTION

The invention disclosed herein provides polynucleotide molecules having gene regulatory activity identified from the transcription factor Nuclear Factor B (NFB2) gene of *Zea mays*. The design, construction, and use of these polynucleotide molecules are one object of this invention. The polynucleotide sequences of these polynucleotide molecules are provided as SEQ ID NO: 1 through SEQ ID NO: 5. These polynucleotide molecules are capable of affecting the expression of an operably linked transcribable polynucleotide molecule in plant tissues and therefore can selectively regulate gene expression in transgenic plants. The present invention also provides methods of modifying, producing, and using the same. The invention also includes compositions, transformed host cells, transgenic plants, and seeds containing the promoters, and methods for preparing and using the same.

Polynucleotide Molecules

Many types of regulatory sequences control gene expression. Not all genes are turned on at all times during the life cycle of a plant. Different genes are required for the completion of different steps in the developmental and sexual maturation of the plant. Two general types of control can be described: temporal regulation, in which a gene is only expressed at a specific time in development (for example, during flowering), and spatial regulation, in which a gene is only expressed in a specific location in the plant (for example, seed storage proteins). Many genes, however, may fall into both classes. For example, seed storage proteins are only expressed in the seed, but they also are only expressed during a short period of time during the development of the seed. Furthermore, because the binding of RNA Polymerase II to the promoter is the key step in gene expression, it follows that sequences may exist in the promoter that control temporal and spatial gene expression.

The following definitions and methods are provided to better define the present invention and to guide those of ordinary skill in the art in the practice of the present invention. Unless otherwise noted, terms are to be understood according to conventional usage by those of ordinary skill in the relevant art.

The phrases "coding sequence," "structural sequence," and "transcribable polynucleotide sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and transcribable polynucleotide sequence encode a series of amino acids forming a protein, polypeptide, or peptide sequence. The coding sequence, structural sequence, and transcribable polynucleotide sequence may be contained, without limitation, within a larger nucleic acid molecule, vector, etc. In addition, the orderly arrangement of nucleic acids in these sequences may be depicted, without limitation, in the form of a sequence listing, figure, table, electronic medium, etc.

As used herein, the term "polynucleotide molecule" refers to the single- or double-stranded DNA or RNA molecule of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for nucleotide bases as set forth at 37 CFR §1.822 is used herein.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are polynucleotide molecules having gene regulatory activity which play an integral part in the overall expression of genes in living cells. Isolated regulatory elements that function in plants are therefore useful for modifying plant phenotypes through the methods of genetic engineering. By "regulatory element" it is intended a series of nucleotides that determines if, when, and at what level a particular gene is expressed. The regulatory DNA sequences specifically interact with regulatory proteins or other proteins.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter modulates transcription of the gene of interest in a cell.

As used herein, the term "gene regulatory activity" refers to a polynucleotide molecule capable of affecting transcription or translation of an operably linked polynucleotide molecule. An isolated polynucleotide molecule having gene regulatory activity may provide temporal or spatial expression or modulate levels and rates of expression of the operably linked polynucleotide molecule. An isolated polynucleotide molecule having gene regulatory activity may comprise a promoter, intron, leader, or 3' transcriptional termination region.

As used herein, the term "gene expression" or "expression" refers to the transcription of a DNA molecule into a transcribed RNA molecule. Gene expression may be described as related to temporal, spatial, developmental, or morphological qualities as well as quantitative or qualitative indications. The transcribed RNA molecule may be translated to produce a protein molecule or may provide an antisense or other regulatory RNA molecule.

As used herein, an "expression pattern" is any pattern of differential gene expression. In a preferred embodiment, an expression pattern is selected from the group consisting of tissue, temporal, spatial, developmental, stress, environmental, physiological, pathological, cell cycle, and chemically responsive expression patterns.

As used herein, an "enhanced expression pattern" is any expression pattern for which an operably linked nucleic acid sequence is expressed at a level greater than 0.01%; preferably in a range of about 0.5% to about 20% (w/w) of the total cellular RNA or protein.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule, including but not limited to protein coding sequences (e.g. transgenes) and sequences (e.g. a molecule useful for gene suppression).

The present invention includes a polynucleotide molecule having a nucleic acid sequence that hybridizes to SEQ ID NO: 1 through SEQ ID NO: 5, or any complements thereof, or any cis elements thereof, or any fragments thereof. The present invention also provides a nucleic acid molecule comprising a nucleic acid sequence selected from the group consisting of SEQ ID NO: 1 through SEQ ID NO: 5, any complements thereof, or any cis elements thereof, or any fragments thereof. The polynucleotide molecules of the present invention (SEQ ID NO: 1 through SEQ ID NO: 5) were all isolated or identified from the *Zea mays* NFB2 gene, and are represented in the polynucleotide constructs listed in Table 1.

TABLE 1

Sequence Annotations for Polynucleotide Molecules
Isolated from the NFB2 gene of *Zea mays*

| SEQ ID | Sequence Descriptions | Regulatory Element Types | Nucleotide Positions | Construct (pMON) ID |
|---|---|---|---|---|
| 1 | 5' Expression Element Cassette, comprising: P-Zm.NFB2-1:1:2 L-Zm.NFB2-1:1:1 I-Zm.NFB2-1:1:1 L-Zm.NFB2-1:1:2 | Promoter Leader Intron Leader | 1-1031 | pMON94347 |
| 2 | P-Zm.NFB2-1:1:2 | Promoter | 1-728 | pMON94347 |
| 3 | L-Zm.NFB2-1:1:1 | Leader | 729-912 | pMON94347 |
| 4 | I-Zm.NFB2-1:1:1 | Intron | 913-1017 | pMON94347 |
| 5 | L-Zm.NFB2-1:1:2 | Leader | 1018-1031 | pMON94347 |

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with an incubation at 55° C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

A nucleic acid molecule preferably comprises a nucleic acid sequence that hybridizes, under low or high stringency conditions, with SEQ ID NO: 1 through SEQ ID NO: 5, any complements thereof, or any fragments thereof, or any cis elements thereof. A nucleic acid molecule most preferably comprises a nucleic acid sequence that hybridizes under high stringency conditions with SEQ ID NO: 1 through SEQ ID NO: 5, any complements thereof, or any fragments thereof, or any cis elements thereof.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *Journal of Molecular Biology* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics*, 2:482-489, 1981, Smith et al., *Nucleic Acids Research* 11:2205-2220, 1983). The percent identity is most preferably determined using the "Best Fit" program.

Useful methods for determining sequence identity are also disclosed in Guide to Huge Computers, Martin J. Bishop, ed., Academic Press, San Diego, 1994, and Carillo, H., and Lipton, D., *Applied Math* (1988) 48:1073. More particularly, preferred computer programs for determining sequence identity include the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., *J. Mol. Biol.* 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

In an alternative embodiment, the nucleic acid molecule comprises a nucleic acid sequence that exhibits 70% or greater identity, and more preferably at least 80 or greater, 85 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid molecule selected from the group consisting of SEQ ID NO: 1 through SEQ ID NO: 5, any complements thereof, any fragments thereof, or any cis elements thereof. The nucleic acid molecule preferably comprises a nucleic acid sequence that exhibits a 75% or greater sequence identity with a polynucleotide selected from the group consisting of SEQ ID NO: 1 through SEQ ID NO: 5, any complements thereof, any fragments thereof, or any cis elements thereof. The nucleic acid molecule more preferably comprises a nucleic acid sequence that exhibits an 80% or greater sequence identity with a polynucleotide selected from the group consisting of SEQ ID NO: 1 through SEQ ID NO: 5, any complements thereof, any fragments thereof, or any cis elements thereof. The nucleic acid molecule most preferably comprises a nucleic acid sequence that exhibits an 85% or greater sequence identity with a polynucleotide selected from the group consisting of SEQ ID NO: 1 through SEQ ID NO: 5, any complements thereof, any fragments thereof, or any cis elements thereof.

For purposes of this invention "percent identity" may also be determined using BLASTX version 2.0 for translated nucleotide sequences and BLASTN version 2.0 for polynucleotide sequences. In a preferred embodiment of the present invention, the presently disclosed corn genomic promoter sequences comprise nucleic acid molecules or fragments having a BLAST score of more than 200, preferably a BLAST score of more than 300, and even more preferably a BLAST score of more than 400 with their respective homologues.

Polynucleotide Molecules, Motifs, Fragments, Chimeric Molecules

Nucleic acid molecules of the present invention include nucleic acid sequences that are between about 0.01 Kb and about 50 Kb, more preferably between about 0.1 Kb and about 25 Kb, even more preferably between about 1 Kb and about 10 Kb, and most preferably between about 3 Kb and about 10 Kb, about 3 Kb and about 7 Kb, about 4 Kb and about 6 Kb, about 2 Kb and about 4 Kb, about 2 Kb and about 5 Kb, about 1 Kb and about 5 Kb, about 1 Kb and about 3 Kb, or about 1 Kb and about 2 Kb.

As used herein, the term "fragment" or "fragment thereof" refers to a finite polynucleotide sequence length that comprises at least 25, at least 50, at least 75, at least 85, or at least 95 contiguous nucleotide bases wherein its complete sequence in entirety is identical to a contiguous component of the referenced polynucleotide molecule.

As used herein, the term "chimeric" refers to the product of the fusion of portions of two or more different polynucleotide molecules. As used herein, the term "chimeric" refers to a gene expression element produced through the manipulation of known elements or other polynucleotide molecules. Novel chimeric regulatory elements can be designed or engineered by a number of methods. In one embodiment of the present invention, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

In another embodiment of the present invention, chimeric molecules may combine enhancer domains that can confer or modulate gene expression from one or more promoters, by fusing a heterologous enhancer domain from a first promoter to a second promoter with its own partial or complete regulatory elements. Examples of suitable enhancer domains to be used in the practice of the present invention include, but are not limited to the enhancer domains from promoters such as P-FMV, the promoter from the 35S transcript of the Figwort mosaic virus (described in U.S. Pat. No. 6,051,753, which is incorporated herein by reference) and P-CaMV 35S, the promoter from the 35S RNA transcript of the Cauliflower mosaic virus (described in U.S. Pat. Nos. 5,530,196, 5,424,200, and 5,164,316, all of which are incorporated herein by reference). Construction of chimeric promoters using enhancer domains is described in, for example, U.S. Pat. No. 6,660,911, which is incorporated herein by reference. Thus, the design, construction, and use of chimeric expression elements according to the methods disclosed herein for modulating the expression of operably linked transcribable polynucleotide molecules are encompassed by the present invention.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus, the design, construction, and use of chimeric regulatory elements is one object of this invention.

Regulatory Elements

Gene expression is finely regulated at both the transcriptional and post-transcriptional levels. A spectrum of control regions regulate transcription by RNA polymerase II. Enhancers that can stimulate transcription from a promoter tens of thousands of base pairs away (e.g., the SV40 enhancer) are an example of long-range effectors, whereas more proximal elements include promoters and introns. Transcription initiates at the cap site encoding the first nucleotide of the first exon of an mRNA. For many genes, especially those encoding abundantly expressed proteins, a TATA box located 25-30 base pairs upstream form the cap site directs RNA polymerase II to the start site. Promoter-proximal elements roughly within the first 200 base pairs upstream of the cap site stimulate transcription.

Features of the untranslated regions of mRNAs that control translation, degradation and localization include stem-loop structures, upstream initiation codons and open reading frames, internal ribosome entry sites and various cis-acting elements that are bound by RNA-binding proteins.

The present invention provides the composition and utility of molecules comprising regulatory element sequences identified from *Zea mays*. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a recombinant construct of the present invention.

One skilled in the art would know various promoters, introns, enhancers, transit peptides, targeting signal sequences, 5' and 3' untranslated regions (UTRs), as well as other molecules involved in the regulation of gene expression that are useful in the design of effective plant expression vectors, such as those disclosed, for example, in U.S. Patent Application Publication 2003/01403641 (herein incorporated by reference).

UTRs

UTRs are known to play crucial roles in the post-transcriptional regulation of gene expression, including modulation of the transport of mRNAs out of the nucleus and of translation efficiency, subcellular localization and stability. Regulation by UTRs is mediated in several ways. Nucleotide patterns or motifs located in 5' UTRs and 3' UTRs can interact with specific RNA-binding proteins. Unlike DNA-mediated regulatory signals, however, whose activity is essentially mediated by their primary structure, the biological activity of regulatory motifs at the RNA level relies on a combination of primary and secondary structure. Interactions between sequence elements located in the UTRs and specific complementary RNAs have also been shown to play key regulatory roles. Finally, there are examples of repetitive elements that are important for regulation at the RNA level, affecting translation efficiency.

For example, non-translated 5' leader polynucleotide molecules derived from heat shock protein genes have been demonstrated to enhance gene expression in plants (see for example, U.S. Pat. No. 5,659,122 and U.S. Pat. No. 5,362,865, all of which are incorporated herein by reference).

Cis-Acting Elements

Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation. Cis elements occur within the 5' UTR associated with a particular coding sequence, and are often found within promoters and promoter modulating sequences (inducible elements). Cis elements can be identified using known cis elements as a target sequence or target motif in the BLAST programs of the present invention. Examples of cis-acting elements in the 5'UTR associated with a polynucleotide coding sequence include, but are not limited to, promoters and enhancers.

Promoters

Among the gene expression regulatory elements, the promoter plays a central role. Along the promoter, the transcription machinery is assembled and transcription is initiated. This early step is often rate-limiting relative to subsequent stages of protein production. Transcription initiation at the promoter may be regulated in several ways. For example, a promoter may be induced by the presence of a particular compound or external stimuli, express a gene only in a specific tissue, express a gene during a specific stage of development, or constitutively express a gene. Thus, transcription of a transgene may be regulated by operably linking the coding sequence to promoters with different regulatory characteristics. Accordingly, regulatory elements such as promoters, play a pivotal role in enhancing the agronomic, pharmaceutical or nutritional value of crops.

As used herein, the term "promoter" refers to a polynucleotide molecule that is involved in recognition and binding of RNA polymerase II and other proteins such as transcription factors (trans-acting protein factors that regulate transcription) to initiate transcription of an operably linked gene. A promoter may be isolated from the 5' untranslated region (5' UTR) of a genomic copy of a gene. Alternately, promoters may be synthetically produced or manipulated DNA elements. Promoters may be defined by their temporal, spatial, or developmental expression pattern. A promoter can be used as a regulatory element for modulating expression of an operably linked transcribable polynucleotide molecule. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

Any of the nucleic acid molecules described herein may comprise nucleic acid sequences comprising promoters. Promoters of the present invention can include between about 300 bp upstream and about 10 kb upstream of the trinucleotide ATG sequence at the start site of a protein coding region. Promoters of the present invention can preferably include between about 300 bp upstream and about 5 kb upstream of the trinucleotide ATG sequence at the start site of a protein coding region. Promoters of the present invention can more preferably include between about 300 bp upstream and about 2 kb upstream of the trinucleotide ATG sequence at the start site of a protein coding region. Promoters of the present invention can include between about 300 bp upstream and about 1 kb upstream of the trinucleotide ATG sequence at the start site of a protein coding region. While in many circumstances a 300 bp promoter may be sufficient for expression, additional sequences may act to further regulate expression, for example, in response to biochemical, developmental or environmental signals.

The promoter of the present invention preferably transcribes a heterologous transcribable polynucleotide sequence at a high level in a plant. More preferably, the promoter hybridizes to a nucleic acid sequence selected from the group consisting of SEQ ID NO: 1 through SEQ ID NO: 5, or any complements thereof, or any fragments thereof. Suitable hybridization conditions include those described above. A nucleic acid sequence of the promoter preferably hybridizes, under low or high stringency conditions, with SEQ ID NOs: 1 or 2, or any complements thereof, or any fragments thereof, or any cis elements thereof.

In an alternative embodiment, the promoter comprises a nucleic acid sequence that exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid sequence selected from the group consisting of SEQ ID NO: 1 through SEQ ID NO: 5, or complements thereof. The promoter most preferably comprises a nucleic acid sequence selected from the group consisting of SEQ ID NOs: 1 or 2, any complements thereof, or any fragments thereof, or any cis elements thereof.

A promoter comprises promoter fragments that have promoter activity. Promoter fragments may comprise other regulatory elements such as enhancer domains, and may further be useful for constructing chimeric molecules. Fragments of SEQ ID NO: 1 comprise at least about 50, 95, 150, 250, 350, 400, 450, 500, 750 or 1000 contiguous nucleotides of the polynucleotide sequence of SEQ ID NO: 1, up to the full 1031 nucleotides of SEQ ID NO: 1. Fragments of SEQ ID NO: 2 comprise at least about 50, 95, 150, 250, 350, 400, 450, 500, 550, 600 or 700 contiguous nucleotides of the polynucleotide sequence of SEQ ID NO: 2, up to the full 728 nucleotides of SEQ ID NO: 2.

At least two types of information are useful in predicting promoter regions within a genomic DNA sequence. First, promoters may be identified on the basis of their sequence "content," such as transcription factor binding sites and various known promoter motifs. (Stormo, Genome Research 10: 394-397 (2000)). Such signals may be identified by computer programs that identify sites associated with promoters, such as TATA boxes and transcription factor (TF) binding sites. Second, promoters may be identified on the basis of their "location," i.e. their proximity to a known or suspected coding sequence. (Stormo, Genome Research 10: 394-397 (2000)). Promoters are typically found within a region of DNA extending approximately 150-1500 basepairs in the 5' direction from the start codon of a coding sequence. Thus, promoter regions may be identified by locating the start codon of a coding sequence, and moving beyond the start codon in the 5' direction to locate the promoter region.

Promoter sequence may be analyzed for the presence of common promoter sequence characteristics, such as a TATA-box and other known transcription factor binding site motifs. These motifs are not always found in every known promoter, nor are they necessary for promoter function, but when present, do indicate that a segment of DNA is a promoter sequence.

For identification of the TATA-box, the putative promoter sequences immediately upstream of the coding start site of the predicted genes within a given sequence size range, as described above, are used. The transcription start site and TATA-box (if present) may be predicted with program TSSP. TSSP is designed for predicting PolII promoter regions in plants, and is based on the discriminate analysis combing characteristics of functional elements of regulatory sequence with the regulatory motifs from Softberry Inc.'s plant RegSite database (Solovyev V. V. (2001) *Statistical approaches in Eukaryotic gene prediction*. In: Handbook of Statistical genetics (eds. Balding D. et al.), John Wiley & Sons, Ltd., p. 83-127). In the cases that multiple TATA-boxes are predicted, only the rightmost (closest to the 5' end) TATA-box is kept. The transcription start sites (TSS) are refined and extended upstream, based on the matches to the database sequences. Promoter sequences with unique TATA-box, as well as the TATA-box locations, may be identified within the promoter sequences.

For identification of other known transcription factor binding motifs (such as a GC-box, CAAT-box, etc.), the promoter sequences immediately upstream of the coding start site of the predicted genes within a given sequence size range, as described above, are used. The known transcription factor binding motifs (except TATA-box) on the promoter sequences are predicted with a proprietary program PromoterScan. The identification of such motifs provide important information about the candidate promoter. For example, some motifs are associated with informative annotations such as (but not limited to) "light inducible binding site" or "stress inducible binding motif" and can be used to select with confidence a promoter that is able to confer light inducibility or stress inducibility to an operably-linked transgene, respectively.

Putative promoter sequences are also searched with matcorns for the GC box (factor name: V_GC_01) and CCAAT box (factor name: F_HAP234_01). The matcorns for the GC box and the CCAAT box are from Transfac. The algorithm that is used to annotate promoters searches for matches to both sequence motifs and matrix motifs. First, individual matches are found. For sequence motifs, a maximum number of mismatches are allowed. If the code M, R, W, S, Y, or K are listed in the sequence motif (each of which is a degenerate code for 2 nucleotides) ½ mismatch is allowed. If the code B, D, H, or V is listed in the sequence motif (each of which is a degenerate code for 3 nucleotides) ⅓ mismatch is allowed. Appropriate p values may be determined by simulation by generation of a 5 Mb length of random DNA with the same dinucleotide frequency as the test set, and from this test set the probability of a given matrix score was determined (number of hits/5e7). Once the individual hits are found, the putative promoter sequence is searched for clusters of hits in a 250 bp window. The score for a cluster is found by summing the negative natural log of the p value for each individual hit. Using simulations with 100 Mb lengths, the probability of a window having a cluster score greater than or equal to the given value is determined. Clusters with a p value more significant than p<1e-6 are reported. Effects of repetitive elements are screened. For matrix motifs, a p value cutoff is used on a matrix score. The matrix score is determined by adding the path of a given DNA sequence through a matrix. Appropriate p values are determined by simulation: 5 Mb lengths of random DNA with the same dinucleotide frequency as a test set are generated to test individual matrix hits, and 100 Mb lengths are used to test clusters. The probability of a given matrix score and the probability scores for clusters are determined, as are the sequence motifs. The usual cutoff for matcorns is 2.5e-4. No clustering was done for the GC box or CAAT box.

Examples of promoters include: those described in U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter, P-Zm.L3), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gama-coixin promoter, P-Cl.Gcx), and U.S. patent application Ser. No. 09/757,089 (maize chloroplast aldolase promoter), all of which are incorporated herein by reference in their entirety.

Promoters of the present invention include homologues of cis elements known to effect gene regulation that show homology with the promoter sequences of the present invention. These cis elements include, but are not limited to, oxygen responsive cis elements (Cowen et al., J. Biol. Chem. 268(36):26904-26910 (1993)), light regulatory elements (Bruce and Quaill, Plant Cell 2 (11):1081-1089 (1990); Bruce et al., EMBO J. 10:3015-3024 (1991); Rocholl et al., Plant Sci. 97:189-198 (1994); Block et al., Proc. Natl. Acad. Sci. USA 87:5387-5391 (1990); Giuliano et al., Proc. Natl. Acad. Sci. USA 85:7089-7093 (1988); Staiger et al., Proc. Natl. Acad. Sci. USA 86:6930-6934 (1989); Izawa et al., Plant Cell 6:1277-1287 (1994); Menkens et al., Trends in Biochemistry 20:506-510 (1995); Foster et al., FASEB J. 8:192-200 (1994); Plesse et al., Mol Gen Gene 254:258-266 (1997); Green et al., EMBO J. 6:2543-2549 (1987); Kuhlemeier et al., Ann. Rev Plant Physiol. 38:221-257 (1987); Villain et al., J. Biol. Chem. 271:32593-32598 (1996); Lam et al., Plant Cell 2:857-866 (1990); Gilmartin et al., Plant Cell 2:369-378 (1990); Datta et al., Plant Cell 1:1069-1077 (1989); Gilmartin et al., Plant Cell 2:369-378 (1990); Castresana et al., EMBO J. 7:1929-1936 (1988); Ueda et al., Plant Cell 1:217-227 (1989); Terzaghi et al., Annu. Rev. Plant Physiol. Plant Mol. Biol. 46:445-474 (1995); Green et al., EMBO J. 6:2543-2549 (1987); Villain et al., J. Biol. Chem. 271:32593-32598 (1996); Tjaden et al., Plant Cell 6:107-118 (1994); Tjaden et al., Plant Physiol. 108:1109-1117 (1995); Ngai et al., Plant J. 12:1021-1234 (1997); Bruce et al., EMBO J. 10:3015-3024 (1991); Ngai et al., Plant J. 12:1021-1034 (1997)), elements responsive to gibberellin, (Muller et al., J. Plant Physiol. 145:606-613 (1995); Croissant et al., Plant Science 116:27-35 (1996); Lohmer et al., EMBO J. 10:617-624 (1991); Rogers et al., Plant Cell 4:1443-1451 (1992); Lanahan et al., Plant Cell 4:203-211 (1992); Skriver et al., Proc. Natl. Acad. Sci. USA 88:7266-7270 (1991); Gilmartin et al., Plant Cell 2:369-378 (1990); Huang et al., Plant Mol. Biol. 14:655-668 (1990); Gubler et al., Plant Cell 7:1879-1891 (1995)), elements responsive to abscisic acid, (Busk et al., Plant Cell 9:2261-2270 (1997); Guiltinan et al., Science 250:267-270 (1990); Shen et al., Plant Cell 7:295-307 (1995); Shen et al., Plant Cell 8:1107-1119 (1996); Seo et al., Plant Mol. Biol. 27:1119-1131 (1995); Marcotte et al., Plant Cell 1:969-976 (1989); Shen et al., Plant Cell 7:295-307 (1995); Iwasaki et al., Mol Gen Genet. 247:391-398 (1995); Hattori et al., Genes Dev. 6:609-618 (1992); Thomas et al., Plant Cell 5:1401-1410 (1993)), elements similar to abscisic acid responsive elements, (Ellerstrom et al., Plant Mol. Biol. 32:1019-1027 (1996)), auxin responsive elements (Liu et al., Plant Cell 6:645-657 (1994); Liu et al., Plant Physiol. 115:397-407 (1997); Kosugi et al., Plant J. 7:877-886 (1995); Kosugi et al., Plant Cell 9:1607-1619 (1997); Ballas et al., J. Mol. Biol. 233:580-596 (1993)), a cis element responsive to methyl jasmonate treatment (Beaudoin and Rothstein, Plant Mol. Biol. 33:835-846 (1997)), a cis element responsive to abscisic acid and stress response (Straub et al., Plant Mol. Biol. 26:617-630 (1994)), ethylene responsive cis elements (Itzhaki et al., Proc. Natl. Acad. Sci. USA 91:8925-8929 (1994); Montgomery et al., Proc. Natl. Acad. Sci. USA 90:5939-5943 (1993); Sessa et al., Plant Mol. Biol. 28:145-153 (1995); Shinshi et al., Plant Mol. Biol. 27:923-932 (1995)), salicylic acid cis responsive elements, (Strange et al., Plant J. 11:1315-1324 (1997); Qin et al., Plant Cell 6:863-874 (1994)), a cis element that responds to water stress and abscisic acid (Lam et al., J. Biol. Chem. 266:17131-17135 (1991); Thomas et al., Plant Cell 5:1401-1410 (1993); Pla et al., Plant Mol Biol 21:259-266 (1993)), a cis element essential for M phase-specific expression (Ito et al., Plant Cell 10:331-341 (1998)), sucrose responsive elements (Huang et al., Plant Mol. Biol. 14:655-668 (1990); Hwang et al., Plant Mol Biol 36:331-341 (1998); Grierson et al., Plant J. 5:815-826 (1994)), heat shock response elements (Pelham et al., Trends Genet. 1:31-35 (1985)), elements responsive to auxin and/or salicylic acid and also reported for light regulation (Lam et al., Proc. Natl. Acad. Sci. USA 86:7890-7897 (1989); Benfey et al., Science 250:959-966 (1990)), elements responsive to ethylene and salicylic acid (Ohme-Takagi et al., Plant Mol. Biol. 15:941-946 (1990)), elements responsive to wounding and abiotic stress (Loake et al., Proc. Natl. Acad. Sci. USA 89:9230-9234 (1992); Mhiri et al., Plant Mol. Biol. 33:257-266 (1997)), antioxidant response elements (Rushmore et al., J. Biol. Chem. 266:11632-11639; Dalton et al., Nucleic Acids Res. 22:5016-5023 (1994)), Sph elements (Suzuki et al., Plant Cell 9:799-807 1997)), elicitor responsive elements, (Fukuda et al., Plant Mol. Biol. 34:81-87 (1997); Rushton et al., EMBO J. 15:5690-5700 (1996)), metal responsive elements (Stuart et al., Nature 317:828-831 (1985); Westin et al., EMBO J. 7:3763-3770 (1988); Thiele et al., Nucleic Acids Res. 20:1183-1191 (1992); Faisst et al., Nucleic Acids Res. 20:3-26 (1992)), low temperature responsive elements, (Baker et al., Plant Mol. Biol. 24:701-713 (1994); Jiang et al., Plant Mol. Biol. 30:679-684 (1996); Nordin et al., Plant Mol. Biol. 21:641-653 (1993); Zhou et al., J. Biol. Chem. 267: 23515-23519 (1992)), drought responsive elements, (Yamaguchi et al., Plant Cell 6:251-264 (1994); Wang et al., Plant Mol. Biol. 28:605-617 (1995); Bray E A, Trends in Plant Science 2:48-54 (1997)) enhancer elements for glutenin, (Colot et al., EMBO J. 6:3559-3564 (1987); Thomas et al., Plant Cell 2:1171-1180 (1990); Kreis et al., Philos. Trans. R. Soc. Lond., B314:355-365 (1986)), light-independent regulatory elements, (Lagrange et al., Plant Cell 9:1469-1479 (1997); Villain et al., J. Biol. Chem. 271:32593-32598 (1996)), OCS enhancer elements, (Bouchez et al., EMBO J. 8:4197-4204 (1989); Foley et al., Plant J. 3:669-679 (1993)), ACGT elements, (Foster et al., FASEB J. 8:192-200 (1994); Izawa et al., Plant Cell 6:1277-1287 (1994); Izawa et al., J. Mol. Biol. 230:1131-1144 (1993)), negative cis elements in plastid related genes, (Zhou et al., J. Biol. Chem. 267:23515-23519 (1992); Lagrange et al., Mol. Cell. Biol. 13:2614-2622 (1993); Lagrange et al., Plant Cell 9:1469-1479 (1997); Zhou et al., J. Biol. Chem. 267:23515-23519 (1992)), prolamin box elements, (Forde et al., Nucleic Acids Res. 13:7327-7339 (1985); Colot et al., EMBO J. 6:3559-3564 (1987); Thomas et al., Plant Cell 2:1171-1180 (1990); Thompson et al., Plant Mol. Biol. 15:755-764 (1990); Vicente et al., Proc. Natl. Acad. Sci. USA 94:7685-7690 (1997)), elements in enhancers from the IgM heavy chain gene (Gillies et al., Cell 33:717-728 (1983); Whittier et al., Nucleic Acids Res. 15:2515-2535 (1987)).

The activity or strength of a promoter may be measured in terms of the amount of mRNA or protein accumulation it specifically produces, relative to the total amount of mRNA or protein. The promoter preferably expresses an operably linked nucleic acid sequence at a level greater than 0.01%; preferably in a range of about 0.5% to about 20% (w/w) of the total cellular RNA or protein.

Alternatively, the activity or strength of a promoter may be expressed relative to a well-characterized promoter (for which transcriptional activity was previously assessed). For example, a less-characterized promoter may be operably linked to a reporter sequence (e.g., GUS) and introduced into a specific cell type. A well-characterized promoter (e.g. the 35S promoter) is similarly prepared and introduced into the same cellular context. Transcriptional activity of the unknown promoter is determined by comparing the amount of reporter expression, relative to the well characterized promoter. In one embodiment, the activity of the present promoter is as strong as the 35S promoter when compared in the same cellular context. The cellular context is preferably maize, sorghum, corn, barley, wheat, canola, soybean, or maize; and more preferably is maize, sorghum, corn, barley, or wheat; and most preferably is soybean or maize.

Enhancers

Enhancers, which strongly activate transcription, frequently in a specific differentiated cell type, are usually 100-200 base pairs long. Although enhancers often lie within a few kilobases of the cap site, in some cases they lie much further upstream or downstream from the cap site or within an intron.

Some genes are controlled by more than one enhancer region, as in the case of the *Drosophila* even-skipped gene.

As used herein, the term "enhancer domain" refers to a cis-acting transcriptional regulatory element (cis-element), which confers an aspect of the overall modulation of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation.

Translational enhancers may also be incorporated as part of a recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Examples of other regulatory element 5' nucleic acid leader sequences include dSSU 5', PetHSP70 5', and GmHSP17.9 5'. A translational enhancer sequence derived from the untranslated leader sequence from the mRNA of the coat protein gene of alfalfa mosaic virus coat protein gene, placed between the promoter and the gene, to increase translational efficiency, is described in U.S. Pat. No. 6,037,527, herein incorporated by reference. Thus, the design, construction, and use of enhancer domains according to the methods disclosed herein for modulating the expression of operably linked transcribable polynucleotide molecules are encompassed by the present invention.

Any of the polynucleotide molecules of the present invention may comprise an enhancer.

Leaders

As used herein, the term "leader" refers to a polynucleotide molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A "plant leader" is a native or non-native leader that is functional in plant cells. A plant leader can be used as a 5' regulatory element for modulating expression of an operably linked transcribable polynucleotide molecule.

For example, non-translated 5' leader polynucleotide molecules derived from heat shock protein genes have been demonstrated to enhance gene expression in plants (see for example, U.S. Pat. No. 5,659,122 and U.S. Pat. No. 5,362,865, all of which are incorporated herein by reference). The leaders of the present invention are preferably given as SEQ ID NOs: 3 and 5.

Any of the nucleic acid molecules described herein may comprise nucleic acid sequences comprising leaders. A leader of the present invention preferably assists in the regulation of transcription of a heterologous transcribable polynucleotide sequence at a high level in a plant. Preferably, the leader hybridizes to a nucleic acid sequence selected from the group consisting of SEQ ID NO: 1 through SEQ ID NO: 5, or any complements thereof, or any fragments thereof. Suitable hybridization conditions include those described above. A nucleic acid sequence of the leader more preferably hybridizes, under low or high stringency conditions, with SEQ ID NOs: 1, 3 or 5, or any complements thereof, or any fragments thereof. The leader most preferably hybridizes under high stringency conditions to a nucleic acid sequence selected from the group consisting of SEQ ID NOs 1, 3 or 5, or any complements thereof, or any fragments thereof.

In an alternative embodiment, the leader comprises a nucleic acid sequence that exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid sequence selected from the group consisting of SEQ ID NO: 1 through SEQ ID NO: 5, or complements thereof. The leader most preferably comprises a nucleic acid sequence selected from the group consisting of SEQ ID NOs 1, 3 or 5, any complements thereof, or any fragments thereof.

Introns

As used herein, the term "intron" refers to a polynucleotide molecule that may be isolated or identified from the intervening sequence of a genomic copy of a gene and may be defined generally as a region spliced out during mRNA processing prior to translation. Alternately, introns may be synthetically produced or manipulated DNA elements. Introns may themselves contain sub-elements such as cis-elements or enhancer domains that effect the transcription of operably linked genes. A "plant intron" is a native or non-native intron that is functional in plant cells. A plant intron may be used as a regulatory element for modulating expression of an operably linked gene or genes. A polynucleotide molecule sequence in a recombinant construct may comprise introns. The introns may be heterologous with respect to the transcribable polynucleotide molecule sequence.

The transcribable polynucleotide molecule sequence in the recombinant vector may comprise introns. The introns may be heterologous with respect to the transcribable polynucleotide molecule sequence. Examples of regulatory element introns include the corn actin intron and the corn HSP70 intron (U.S. Pat. No. 5,859,347, herein incorporated by reference in its entirety).

Any of the molecule of the present invention may comprise introns. The intron of the present invention preferably transcribes a heterologous transcribable polynucleotide sequence at a high level in a plant. More preferably, the intron hybridizes to a nucleic acid sequence selected from the group consisting of SEQ ID NO: 1 through SEQ ID NO: 5, or any complements thereof, or any fragments thereof. Suitable hybridization conditions include those described above. A nucleic acid sequence of the intron preferably hybridizes, under low or high stringency conditions, with SEQ ID NOs: 1 or 4, or any complements thereof, or any fragments thereof.

In an alternative embodiment, the promoter comprises a nucleic acid sequence that exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid sequence selected from the group consisting of SEQ ID NO: 1 through SEQ ID NO: 5, or complements thereof. The intron most preferably comprises a nucleic acid sequence selected from the group consisting of SEQ ID NOs: 1 or 4, any complements thereof, or any fragments thereof.

A intron comprises intron fragments that may have intron activity. Fragments of SEQ ID NO: 4 comprise at least about 25, 50, 75 or 100 contiguous nucleotides of the polynucleotide sequence of SEQ ID NO: 4, up to the full 105 nucleotides of SEQ ID NO: 4.

Terminators

The 3' untranslated regions (3' UTRs) of mRNAs are generated by specific cleavage and polyadenylation. A 3' polyadenylation region means a DNA molecule linked to and located downstream of a structural polynucleotide molecule and includes polynucleotides that provide a polyadenylation signal and other regulatory signals capable of affecting transcription, mRNA processing or gene expression. PolyA tails are thought to function in mRNA stability and in initiation of translation.

As used herein, the term "terminator" refers to a polynucleotide sequence that may be isolated or identified from the 3' untranslated region (3'UTR) of a transcribable gene, which functions to signal to RNA polymerase the termination of transcription. The polynucleotide sequences of the present invention may comprise terminator sequences.

Polyadenylation is the non-templated addition of a 50 to 200 nt chain of polyadenylic acid (polyA). Cleavage must precede polyadenylation. The polyadenylation signal functions in plants to cause the addition of polyadenylate nucleotides to the 3' end of the mRNA precursor. The polyadenylation sequence can be derived from the natural gene, from a variety of plant genes, or from *Agrobacterium* T-DNA genes. Transcription termination often occurs at sites considerably downstream of the sites that, after polyadenylation, are the 3' ends of most eukaryotic mRNAs.

Examples of 3' UTR regions are the nopaline synthase 3' region (nos 3'; Fraley, et al., *Proc. Natl. Acad. Sci.* USA 80: 4803-4807, 1983), wheat hsp17 (T-Ta.Hsp17), and T-Ps.R-bcS2:E9 (pea rubisco small subunit), those disclosed in WO0011200A2 (herein incorporated by reference) and other 3' UTRs known in the art can be tested and used in combination with a DHDPS or AK coding region, herein referred to as T-3'UTR. Another example of terminator regions is given in U.S. Pat. No. 6,635,806, herein incorporated by reference.

Any of the polynucleotide molecules of the present invention may comprise a terminator.

Regulatory Element Isolation and Modification

Any number of methods well known to those skilled in the art can be used to isolate a polynucleotide molecule, or fragment thereof, disclosed in the present invention. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic DNA by designing oligonucleotide primers based on available sequence information and using PCR techniques.

As used herein, the term "isolated polynucleotide molecule" refers to a polynucleotide molecule at least partially separated from other molecules normally associated with it in its native state. In one embodiment, the term "isolated" is also used herein in reference to a polynucleotide molecule that is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed. Use of these probes may greatly facilitate the identification of transgenic plants which contain the presently disclosed nucleic acid molecules. The probes may also be used to screen cDNA or genomic libraries for additional nucleic acid sequences related or sharing homology to the presently disclosed promoters and transcribable polynucleotide sequences. The short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www.genome.wi.mit.edu/cgi-bin/primer/primer3.cgi), STSPipeline (www-genome.wi.mit.edu/cgi-bin/www.STS_Pipeline), or GeneUp (Pesole, et al., *BioTechniques* 25:112-123, 1998), for example, can be used to identify potential PCR primers.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g. related nucleic acid sequences from other species).

The primer or probe is generally complementary to a portion of a nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long. The primer or probe may be prepared by direct chemical synthesis, by PCR (See, for example, U.S. Pat. Nos. 4,683,195, and 4,683,202, each of which is herein incorporated by reference), or by excising the nucleic acid specific fragment from a larger nucleic acid molecule.

Transcribable Polynucleotide Molecules

A regulatory element of the present invention may be operably linked to a transcribable polynucleotide sequence that is heterologous with respect to the regulatory element. The term "heterologous" refers to the relationship between two or more nucleic acid or protein sequences that are derived from different sources. For example, a promoter is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

The transcribable polynucleotide molecule may generally be any nucleic acid sequence for which an increased level of transcription is desired. Alternatively, the regulatory element and transcribable polynucleotide sequence may be designed to down-regulate a specific nucleic acid sequence. This is typically accomplished by linking the promoter to a transcribable polynucleotide sequence that is oriented in the antisense direction. One of ordinary skill in the art is familiar with such antisense technology. Briefly, as the antisense nucleic acid sequence is transcribed, it hybridizes to and sequesters a complimentary nucleic acid sequence inside the cell. This duplex RNA molecule cannot be translated into a protein by the cell's translational machinery. Any nucleic acid sequence may be negatively regulated in this manner.

A regulatory element of the present invention may also be operably linked to a modified transcribable polynucleotide molecule that is heterologous with respect to the promoter. The transcribable polynucleotide molecule may be modified to provide various desirable features. For example, a transcribable polynucleotide molecule may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Due to the degeneracy of the genetic code, different nucleotide codons may be used to code for a particular amino acid. A host cell often displays a preferred pattern of codon usage. Transcribable polynucleotide molecules are preferably constructed to utilize the codon usage pattern of the particular host cell. This generally enhances the expression of the transcribable polynucleotide sequence in a transformed host cell. Any of the above described nucleic acid and amino acid sequences may be modified to reflect the preferred codon usage of a host cell or organism in which they are contained. Modification of a transcribable polynucleotide sequence for optimal codon usage in plants is described in U.S. Pat. No. 5,689,052, herein incorporated by reference.

Additional variations in the transcribable polynucleotide molecules may encode proteins having equivalent or superior characteristics when compared to the proteins from which they are engineered. Mutations may include, but are not limited to, deletions, insertions, truncations, substitutions, fusions, shuffling of motif sequences, and the like. Mutations to a transcribable polynucleotide molecule may be introduced in either a specific or random manner, both of which are well known to those of skill in the art of molecular biology.

Thus, one embodiment of the invention is a regulatory element such as provided in SEQ ID NO: 1 through SEQ ID NO: 5, operably linked to a transcribable polynucleotide molecule so as to modulate transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Genes of Agronomic Interest

The transcribable polynucleotide molecule preferably encodes a polypeptide that is suitable for incorporation into the diet of a human or an animal. Specifically, such transcribable polynucleotide molecules comprise genes of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. Suitable transcribable polynucleotide molecules include but are not limited to those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, or an insecticidal protein.

In one embodiment of the invention, a polynucleotide molecule as shown in SEQ ID NO: 1 through SEQ ID NO: 5, or complements thereof, or fragments thereof, or cis elements thereof comprising regulatory elements is incorporated into a construct such that a polynucleotide molecule of the present invention is operably linked to a transcribable polynucleotide molecule that is a gene of agronomic interest.

The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. Nos. RE37,543; 6,228,623;

5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). The genetic elements, methods, and transgenes described in the patents listed above are incorporated herein by reference.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest may be useful for the practice of the present invention.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670, which is incorporated herein by reference), green fluorescent protein (GFP described in U.S. Pat. No. 5,491,084 and U.S. Pat. No. 6,146,826, all of which are incorporated herein by reference), proteins that confer antibiotic resistance, or proteins that confer herbicide tolerance. Marker genes in genetically modified plants are generally of two types: genes conferring antibiotic resistance or genes conferring herbicide tolerance.

Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

Herbicides for which transgenic plant tolerance has been demonstrated and the method of the present invention can be applied, include but are not limited to: glyphosate, glufosinate, sulfonylureas, imidazolinones, bromoxynil, delapon, dicamba, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. No. 5,627,061, U.S. Pat. No. 5,633,435, U.S. Pat. No. 6,040,497 and in U.S. Pat. No. 5,094,945 for glyphosate tolerance, all of which are incorporated herein by reference); polynucleotides encoding a glyphosate oxidoreductase and a glyphosate-N-acetyl transferase (GOX described in U.S. Pat. No. 5,463,175 and GAT described in U.S. Patent publication 20030083480, dicamba monooxygenase U.S. Patent publication 20030135879, all of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; and the bar gene described in DeBlock, et al. (1987) *EMBO J.* 6:2513-2519 for glufosinate and bialaphos tolerance. The regulatory elements of the present invention can express transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR—S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Constructs and Vectors

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permit the integration of the T-DNA into the genome of a plant cell (see for example U.S. Pat. No. 6,603,061, herein incorporated by reference in its entirety). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908, 4,940,835, 4,769,061 and 4,757,011, all of which are herein incorporated by reference in their entirety. These type of vectors have also been reviewed (Rodriguez, et al. Vectors: A Survey of Molecular Cloning Vectors and Their Uses, Butterworths, Boston, 1988; Glick et al., Methods in Plant Molecular Biology and Biotechnology, CRC Press, Boca Raton, Fla., 1993). Typical vectors useful for expression of nucleic acids in higher plants are well known in the art and include vectors derived from the tumor-inducing (Ti) plasmid of *Agrobacterium tumefaciens* (Rogers, et al., Meth. In Enzymol, 153: 253-277, 1987). Other recombinant vectors useful for plant transformation, including the pCaMVCN transfer control vector, have also been described (Fromm et al., Proc. Natl. Acad. Sci. USA, 82(17): 5824-5828, 1985).

Regulatory Elements in the Construct

Various untranslated regulatory sequences may be included in the recombinant vector. Any such regulatory sequences may be provided in a recombinant vector with other regulatory sequences. Such combinations can be designed or modified to produce desirable regulatory features. Constructs of the present invention would typically comprise one or more gene expression regulatory elements operably linked to a transcribable polynucleotide molecule operably linked to a 3' transcription termination polynucleotide molecule.

Constructs of the present invention may also include additional 5' untranslated regions (5' UTR) of an mRNA polynucleotide molecule or gene which can play an important role in translation initiation. For example, non-translated 5' leader polynucleotide molecules derived from heat shock protein genes have been demonstrated to enhance gene expression in plants (see for example, U.S. Pat. No. 5,659,122 and U.S. Pat. No. 5,362,865, all of which are incorporated herein by reference). These additional upstream regulatory polynucleotide molecules may be derived from a source that is native or heterologous with respect to the other elements present on the construct.

One or more additional promoters may also be provided in the recombinant vector. These promoters may be operably linked to any of the transcribable polynucleotide sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Promoters which function in bacteria, yeast, and plants are all well taught in the art. The additional promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (Poszkowski, et al., *EMBO J.*, 3: 2719, 1989; Odell, et al., *Nature*, 313:810, 1985; Chau et al., *Science*, 244:174-181. 1989).

Often-used constitutive promoters include the CaMV 35S promoter (Odell, et al., *Nature*, 313: 810, 1985), the enhanced CaMV 35S promoter, the Figwort Mosaic Virus (FMV) promoter (Richins, et al., *Nucleic Acids Res.* 20: 8451, 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams, et al., *Biotechnology* 10:540-543, 1992), induced by application of safeners (substituted benzenesulfonamide herbicides; Hershey and Stoner, *Plant Mol. Biol.* 17: 679-690, 1991), heat-shock promoters (Ou-Lee et al., *Proc. Natl. Acad. Sci. U.S.A.* 83: 6815, 1986; Ainley et al., *Plant Mol. Biol.* 14: 949, 1990), a nitrate-inducible promoter derived from the spinach nitrite reductase transcribable polynucleotide sequence (Back et al., *Plant Mol. Biol.* 17: 9, 1991), hormone-inducible promoters (Yamaguchi-Shinozaki et al., *Plant Mol. Biol.* 15: 905, 1990), and light-inducible promoters associated with the small subunit of RuBP carboxylase and LHCP families (Kuhlemeier et al., *Plant Cell* 1: 471, 1989; Feinbaum et al., *Mol. Gen. Genet.* 226: 449-456, 1991; Weisshaar, et al., *EMBO J.* 10: 1777-1786, 1991; Lam and Chua, *J. Biol. Chem.* 266: 17131-17135, 1990; Castresana et al., *EMBO J.* 7: 1929-1936, 1988; Schulze-Lefert, et al., *EMBO J.* 8: 651, 1989).

Examples of useful tissue-specific, developmentally-regulated promoters include the β-conglycinin 7Sα promoter (Doyle et al., *J. Biol. Chem.* 261: 9228-9238, 1986; Slighton and Beachy, *Planta* 172: 356, 1987), and seed-specific promoters (Knutzon, et al., *Proc. Natl. Acad. Sci. U.S.A.* 89: 2624-2628, 1992; Bustos, et al., *EMBO J.* 10: 1469-1479, 1991; Lam and Chua, *Science* 248: 471, 1991). Plant functional promoters useful for preferential expression in seed plastid include those from plant storage proteins and from proteins involved in fatty acid biosynthesis in oilseeds. Examples of such promoters include the 5' regulatory regions from such transcribable polynucleotide sequences as napin (Kridl et al., *Seed Sci. Res.* 1: 209, 1991), phaseolin, zein, soybean trypsin inhibitor, ACP, stearoyl-ACP desaturase, and oleosin. Seed-specific regulation is discussed in EP 0 255 378.

Another exemplary tissue-specific promoter is the lectin promoter, which is specific for seed tissue. The Lectin protein in soybean seeds is encoded by a single transcribable polynucleotide sequence (Le1) that is only expressed during seed maturation and accounts for about 2 to about 5% of total seed mRNA. The lectin transcribable polynucleotide sequence and seed-specific promoter have been fully characterized and used to direct seed specific expression in transgenic tobacco plants (Vodkin, et al., *Cell,* 34: 1023, 1983; Lindstrom, et al., *Developmental Genetics,* 11: 160, 1990).

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel, et al., *Plant Mol. Biol,* 29: 995-1004, 1995); corn sucrose synthetase 1 (Yang, et al., *Proc. Natl. Acad. Sci. USA,* 87: 4144-48, 1990); corn alcohol dehydrogenase 1 (Vogel, et al., *J. Cell Biochem.,* (Suppl) 13D: 312, 1989); corn light harvesting complex (Simpson, *Science,* 233: 34, 1986); corn heat shock protein (Odell, et al., *Nature,* 313: 810, 1985); the chitinase promoter from *Arabidopsis* (Samac, et al., *Plant Cell,* 3:1063-1072, 1991); the LTP (Lipid Transfer Protein) promoters from broccoli (Pyee, et al., *Plant J.,* 7: 49-59, 1995); petunia chalcone isomerase (Van Tunen, et al., *EMBO J.* 7: 1257, 1988); bean glycine rich protein 1 (Keller, et al., *EMBO L.,* 8: 1309-1314, 1989); Potato patatin (Wenzler, et al., *Plant Mol. Biol.,* 12: 41-50, 1989); the ubiquitin promoter from maize (Christensen et al., *Plant Mol. Biol.,* 18: 675, 689, 1992); and the actin promoter from corn (McElroy, et al., *Plant Cell,* 2:163-171, 1990).

The additional promoter is preferably tissue specific, constitutive, or inducible. The promoter is most preferably the nopaline synthase (NOS), octopine synthase (OCS), mannopine synthase (MAS), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or corn RC2 promoter.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'.

The recombinant vector may further comprise a nucleic acid sequence encoding a transit peptide. This peptide may be useful for directing a protein to the extracellular space, a chloroplast, or to some other compartment inside or outside of the cell (see, e.g., European Patent Application Publication Number 0218571, herein incorporated by reference).

The transcribable polynucleotide sequence in the recombinant vector may comprise introns. The introns may be heterologous with respect to the transcribable polynucleotide sequence. Preferred introns include the corn actin intron and the corn HSP70 intron.

In addition, constructs may include additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). A 3' non-translated region typically provides a transcriptional termination signal, and a polyadenylation signal which functions in plants to cause the addition of adenylate nucleotides to the 3' end of the mRNA. These may be obtained from the 3' regions to the nopaline synthase (nos) coding sequence, the soybean 7Sα storage protein coding sequence, the albumin coding sequence, and the pea ssRUBISCO E9 coding sequence. Particularly preferred 3' nucleic acid sequences include nos 3', E9 3', ADR12 3', 7Sα 3', 11S 3', and albumin 3'. Typically, nucleic acid sequences located a few hundred base pairs downstream of the polyadenylation site serve to terminate transcription. These regions are required for efficient polyadenylation of transcribed mRNA. These additional downstream regulatory polynucleotide molecules may be derived from a source that is native or heterologous with respect to the other elements present on the construct.

Transcribable Polynucleotides in the Construct

The promoter in the recombinant vector is preferably operably linked to a transcribable polynucleotide sequence. Exemplary transcribable polynucleotide sequences, and modified forms thereof, are described in detail above. The promoter of the present invention may be operably linked to a transcribable polynucleotide sequence that is heterologous with respect to the promoter. In one aspect, the transcribable polynucleotide sequence may generally be any nucleic acid sequence for which an increased level of transcription is desired. The transcribable polynucleotide sequence preferably encodes a polypeptide that is suitable for incorporation into the diet of a human or an animal. Suitable transcribable polynucleotide sequences include those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, and an insecticidal protein.

Alternatively, the promoter and transcribable polynucleotide sequence may be designed to down-regulate a specific nucleic acid sequence. This is typically accomplished by linking the promoter to a transcribable polynucleotide sequence that is oriented in the antisense direction. One of ordinary skill in the art is familiar with such antisense technology. Using such an approach, a cellular nucleic acid sequence is effectively down regulated as the subsequent steps of translation are disrupted. Nucleic acid sequences may be negatively regulated in this manner.

Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. No. 5,107,065 and U.S. Pat. No. 5,759,829; posttranscriptional gene suppression using a construct with a sense-oriented transcribable polynucleotide molecule to regulate gene expression in plants is disclosed in U.S. Pat. No. 5,283,184 and U.S. Pat. No. 5,231,020, all of which are hereby incorporated by reference.

Thus, one embodiment of the invention is a construct comprising a regulatory element such as provided in SEQ ID NO: 1 through SEQ ID NO: 5, operably linked to a transcribable polynucleotide molecule so as to modulate transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The constructs of this invention comprising a regulatory element identified or isolated from *Zea mays* may further comprise one or more transcribable polynucleotide molecules. In one embodiment of the invention, a polynucleotide molecule as shown in SEQ ID NO: 1 through SEQ ID NO: 5, or any complements thereof, or any fragments thereof, comprising regulatory elements such as promoters, leaders and chimeric regulatory elements, is incorporated into a construct such that a polynucleotide molecule of the present invention is operably linked to a transcribable polynucleotide molecule that is a selectable marker or a gene of agronomic interest.

The gene regulatory elements of the present invention can be incorporated into a construct using selectable markers and tested in transient or stable plant analyses to provide an indication of the regulatory element's gene expression pattern in stable transgenic plants. Current methods of generating transgenic plants employ a selectable marker gene which is transferred along with any other genes of interest usually on the same DNA molecule. The presence of a suitable marker is necessary to facilitate the detection of genetically modified plant tissue during development.

Thus, in one embodiment of the invention, a polynucleotide molecule of the present invention as shown in SEQ ID NO: 1 through SEQ ID NO: 5, or fragments thereof, or complements thereof, or cis elements thereof is incorporated into a polynucleotide construct such that a polynucleotide molecule of the present invention is operably linked to a transcribable polynucleotide molecule that provides for a selectable, screenable, or scorable marker. The constructs containing the regulatory elements operably linked to a marker gene may be delivered to the tissues and the tissues analyzed by the appropriate mechanism, depending on the marker. The quantitative or qualitative analyses are used as a tool to evaluate the potential expression profile of a regulatory element when operatively linked to a gene of agronomic interest in stable plants. Any marker gene, described above, may be used in a transient assay.

Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Transformation

The invention is also directed to a method of producing transformed cells and plants which comprise, in a 5' to 3' orientation, a gene expression regulatory element operably linked to a heterologous transcribable polynucleotide sequence. Other sequences may also be introduced into the cell, including 3' transcriptional terminators, 3' polyadenylation signals, other translated or untranslated sequences, transit or targeting sequences, selectable markers, enhancers, and operators.

The term "transformation" refers to the introduction of nucleic acid into a recipient host. The term "host" refers to bacteria cells, fungi, animals and animal cells, plants and plant cells, or any plant parts or tissues including protoplasts, calli, roots, tubers, seeds, stems, leaves, seedlings, embryos, and pollen. As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. The term "transgenic" refers to an animal, plant, or other organism containing one or more heterologous nucleic acid sequences.

There are many methods for introducing nucleic acids into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.,* 42: 205, 1991).

Technology for introduction of DNA into cells is well known to those of skill in the art. Methods and materials for transforming plant cells by introducing a plant polynucleotide construct into a plant genome in the practice of this invention can include any of the well-known and demonstrated methods including:

(1) chemical methods (Graham and Van der Eb, *Virology,* 54(2): 536-539, 1973; Zatloukal, et al., *Ann. N.Y. Acad. Sci.,* 660: 136-153, 1992);

(2) physical methods such as microinjection (Capecchi, *Cell,* 22(2): 479-488, 1980), electroporation (Wong and Neumann, *Biochim. Biophys. Res. Commun.,* 107(2): 584-587, 1982; Fromm et al., *Proc. Natl. Acad. Sci. USA,* 82(17): 5824-5828, 1985; U.S. Pat. No. 5,384,253, herein incorporated by reference) particle acceleration (Johnston and Tang, *Methods Cell Biol.,* 43(A): 353-365, 1994; Fynan et al., *Proc. Natl. Acad. Sci. USA,* 90(24): 11478-11482, 1993) and microprojectile bombardment (as illustrated in U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865, all of which are herein incorporated by reference);

(3) viral vectors (Clapp, *Clin. Perinatol.,* 20(1): 155-168, 1993; Lu, et al., *J. Exp. Med.,* 178(6): 2089-2096, 1993; Eglitis and Anderson, *Biotechniques,* 6(7): 608-614, 1988);

(4) receptor-mediated mechanisms (Curiel et al., *Hum. Gen. Ther.,* 3(2):147-154, 1992; Wagner, et al., *Proc. Natl. Acad. Sci. USA,* 89(13): 6099-6103, 1992), and (5) bacterial mediated mechanisms such as *Agrobacterium*-mediated transformation (as illustrated in U.S. Pat. No.

5,824,877; U.S. Pat. No. 5,591,616; U.S. Pat. No. 5,981,840; and U.S. Pat. No. 6,384,301, all of which are herein incorporated by reference);

(6) Nucleic acids can be directly introduced into pollen by directly injecting a plant's reproductive organs (Zhou, et al., *Methods in Enzymology*, 101: 433, 1983; Hess, *Intern Rev. Cytol.*, 107: 367, 1987; Luo, et al., *Plant Mol. Biol. Reporter*, 6: 165, 1988; Pena, et al., *Nature*, 325: 274, 1987).

(7) Protoplast transformation, as illustrated in U.S. Pat. No. 5,508,184 (herein incorporated by reference).

(8) The nucleic acids may also be injected into immature embryos (Neuhaus, et al., *Theor. Appl. Genet.*, 75: 30, 1987).

Any of the above described methods may be utilized to transform a host cell with one or more gene regulatory elements of the present invention and one or more transcribable polynucleotide molecules. Host cells may be any cell or organism such as a plant cell, algae cell, algae, fungal cell, fungi, bacterial cell, or insect cell. Preferred hosts and transformants include cells from: plants, *Aspergillus*, yeasts, insects, bacteria and algae.

The prokaryotic transformed cell or organism is preferably a bacterial cell, even more preferably an *Agrobacterium*, *Bacillus*, *Escherichia*, *Pseudomonas* cell, and most preferably is an *Escherichia coli* cell. Alternatively, the transformed organism is preferably a yeast or fungal cell. The yeast cell is preferably a *Saccharomyces cerevisiae*, *Schizosaccharomyces pombe*, or *Pichia pastoris*. Methods to transform such cells or organisms are known in the art (EP 0238023; Yelton et al., *Proc. Natl. Acad. Sci.* (*U.S.A.*), 81:1470-1474 (1984); Malardier et al., *Gene*, 78:147-156 (1989); Becker and Guarente, In: Abelson and Simon (eds.), *Guide to Yeast Genetics and Molecular Biology, Methods Enzymol.*, Vol. 194, pp. 182-187, Academic Press, Inc., New York; Ito et al., *J. Bacteriology*, 153:163 (1983); Hinnen et al., *Proc. Natl. Acad. Sci.* (*U.S.A.*), 75:1920 (1978); Bennett and LaSure (eds.), *More Gene Manipulations in Fungi*, Academic Press, CA (1991)). Methods to produce proteins of the present invention from such organisms are also known (Kudla et al., *EMBO*, 9:1355-1364 (1990); Jarai and Buxton, *Current Genetics*, 26:2238-2244 (1994); Verdier, *Yeast*, 6:271-297 (1990); MacKenzie et al., *Journal of Gen. Microbiol.*, 139: 2295-2307 (1993); Hartl et al., *TIBS*, 19:20-25 (1994); Bergeron et al., *TIBS*, 19:124-128 (1994); Demolder et al., *J. Biotechnology*, 32:179-189 (1994); Craig, *Science*, 260: 1902-1903 (1993); Gething and Sambrook, *Nature*, 355:33-45 (1992); Puig and Gilbert, *J. Biol. Chem.*, 269:7764-7771 (1994); Wang and Tsou, *FASEB Journal*, 7:1515-1517 (9193); Robinson et al., *Bio/Technology*, 1:381-384 (1994); Enderlin and Ogrydziak, *Yeast*, 10:67-79 (1994); Fuller et al., *Proc. Natl. Acad. Sci.* (*U.S.A.*), 86:1434-1438 (1989); Julius et al., *Cell*, 37:1075-1089 (1984); Julius et al., *Cell*, 32:839-852 (1983)).

Another preferred embodiment of the present invention is the transformation of a plant cell. A plant transformation construct comprising a regulatory element of the present invention may be introduced into plants by any plant transformation method.

Methods for transforming dicotyledons, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908, all of which are herein incorporated by reference); soybean (U.S. Pat. No. 5,569,834; U.S. Pat. No. 5,416,011, all of which are herein incorporated by reference; McCabe, et al., *Biotechnology*, 6: 923, 1988; Christou et al., *Plant Physiol.* 87:671-674 (1988)); *Brassica* (U.S. Pat. No. 5,463,174, herein incorporated by reference); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258 (1995)).

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987)); barley (Wan and Lemaux, *Plant Physiol* 104:37 (1994)); maize (Rhodes et al., *Science* 240: 204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); corn (Toriyama et al., *Theor Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152, herein incorporated by reference).

The regeneration, development, and cultivation of plants from transformed plant protoplast or explants is well taught in the art (Weissbach and Weissbach, *Methods for Plant Molecular Biology*, (Eds.), Academic Press, Inc., San Diego, Calif., 1988; Horsch et al., *Science*, 227: 1229-1231, 1985). In this method, transformants are generally cultured in the presence of a selective media which selects for the successfully transformed cells and induces the regeneration of plant shoots (Fraley et al., *Proc. Natl. Acad. Sci. U.S.A.*, 80: 4803, 1983). These shoots are typically obtained within two to four months.

The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transformed plants are analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of the plants of this invention can be harvested from fertile transgenic plants and be used to grow progeny generations of transformed plants of this invention including hybrid plant lines comprising the construct of this invention and expressing a gene of agronomic interest. The present invention also provides for parts of the plants of the present invention. Plant parts, without limitation, include seed, endosperm, ovule and pollen. In a particularly preferred embodiment of the present invention, the plant part is a seed. The invention also includes and provides transformed plant cells which comprise a nucleic acid molecule of the present invention.

The transgenic plant may pass along the transformed nucleic acid sequence to its progeny. The transgenic plant is preferably homozygous for the transformed nucleic acid sequence and transmits that sequence to all of its offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified.

Each periodical, patent, and other document or reference cited herein is herein incorporated by reference in its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Regulatory elements are isolated from *Zea mays* genomic DNA. All regulatory elements are sub-cloned into a plant transformation vector operably linking the regulatory elements to the *Zea mays* HSP70 intron (1-Zm.DnaK-1:1:1, described in U.S. Pat. No. 5,424,412, which is incorporated herein by reference), the coding region for β-glucuronidase (GUS described in U.S. Pat. No. 5,599,670, which is incorporated herein by reference), and the *Agrobacterium tumefaciens* NOS gene terminator.

Variants of the *Zea mays* transcription factor Nuclear Factor B (NFB2) gene's (referred to herein as Zm.NFB2) regulatory elements were isolated from *Zea mays* genomic DNA using sequence-specific primers and PCR amplification methods. One promoter variant (P-Zm.NFB2-1:1:2 given as SEQ ID NO: 2), two leader variants (L-Zm.NFB2-1:1:1 given as SEQ ID NO: 3 and L-Zm.NFB2-1:1:2 given as SEQ ID NO: 5), and one intron variant (I-Zm.NFB2-1:1:1 given as SEQ ID NO: 4) were isolated and cloned into transformation vectors. Vector pMON94347 (FIG. 1), was used for corn transformation, and comprises SEQ ID NO: 1, which further comprises SEQ ID NOs: 2, 3, 4 and 5.

The present invention thus provides isolated polynucleotide molecules having gene regulatory activity (regulatory elements) and DNA constructs comprising the isolated regulatory elements operably linked to a transcribable polynucleotide molecule.

Example 2

Corn Plant Transformation and GUS Analysis

Corn plants are transformed with plant expression constructs for histochemical GUS analysis in plants. Plants are transformed using methods known to those skilled in the art. Particle bombardment of corn H99 immature zygotic embryos may be used to produce transgenic maize plants. Ears of maize H99 plants are collected 10-13 days after pollination from greenhouse grown plants and sterilized. Immature zygotic embryos of 1.2-1.5 mm are excised from the ear and incubated at 28° C. in the dark for 3-5 days before use as target tissue for bombardment. DNA comprising an isolated expression cassette containing the selectable marker for kanamycin resistance (NPTII gene) and the screenable marker for β-D-Glucuronidase (GUS gene) is gel purified and used to coat 0.6 micron gold particles (Catalog #165-2262 Bio-Rad, Hercules, Calif.) for bombardment. Macro-carriers are loaded with the DNA-coated gold particles (Catalog #165-2335 Bio-Rad, Hercules Calif.). The embryos are transferred onto osmotic medium scutellum side up. A PDS 1000/He biolistic gun is used for transformation (Catalog #165-2257 Bio-Rad, Hercules Calif.). Bombarded immature embryos are cultured and transgenic calli are selected and transferred to tissue formation medium. Transgenic corn plants are regenerated from the transgenic calli and transferred to the greenhouse.

GUS activity is qualitatively and quantitatively measured using methods known to those skilled in the art. Plant tissue samples are collected from the same tissue for both the qualitative and quantitative assays. For qualitative analysis, whole tissue sections are incubated with the GUS staining solution X-Gluc (5-bromo-4-chloro-3-indolyl-β-glucuronide) (1 milligram/milliliter) for an appropriate length of time, rinsed, and visually inspected for blue coloration. For quantitative analysis, total protein is first extracted from each tissue sample. One microgram of total protein is used with the fluorogenic substrate 4-methyleumbelliferyl-β-D-glucuronide (MUG) in a total reaction volume of 50 μl (microliters). The reaction product 4-methylumbelliferone (4-MU) is maximally fluorescent at high pH. Addition of a basic solution of sodium carbonate simultaneously stops the assay and adjusts the pH for quantifying the fluorescent product. Fluorescence is measured with excitation at 365 nm, emission at 445 nm using a Fluoromax-3 with Micromax Reader, with slit width set at excitation 2 nm and emission 3 nm. The GUS activity is expressed as pmole of 4-MU/micrograms of protein/hour (pMole of 4-MU/μg protein/hour).

Example 3

NFB2 Regulatory Element Analysis in Stable Transgenic Corn Plants

Corn plants representing ten F1 events (plants representing an independent event produced from R0 transgenic plants crossed with non-transgenic H99 plants) transformed with pMON94347 (comprising SEQ ID NO: 1, which itself further comprises SEQ IDs NO: 2, 3, 4 and 5) were analyzed for GUS activity as described above. Mean levels of GUS activity (pMole of 4-MU/μg protein/hour) for each stage of plant development and organ tested are provided as mean GUS activity +/− standard error (SE) measurements. Abbreviations include: none detected by visible detection methods (ND), three leaf stage (V3), seven leaf stage (V7), tasseling stage (VT), days after germination (DAG), and days after pollination (DAP) are used. Mean levels of GUS activity (pMole of MU/µg protein/hour) for each stage of plant development and organ tested are provided in Table 2.

TABLE 2

Zm.NFB2 Regulatory Element Expression in Transgenic Corn Plant Tissues

| Stages | Organ | Inducer | Mean ± SE |
|---|---|---|---|
| Imbibed seed | Embryo | — | 56.45 ± 10.79 |
| Imbibed seed | Endosperm | — | 15.48 ± 2.34 |
| 3 DAG | Root | Ctrl | 224.49 ± 44.29 |
| 3 DAG | Root | Cold | 169.12 ± 36.32 |
| V3 | Root | Ctrl | 26.57 ± 8.49 |
| V3 | Root | Cold | 14.09 ± 11.19 |
| V3 | Root | Des1 | 13.43 ± 0.00 |
| V3 | Root | Des2 | 90.48 ± 38.62 |
| V3 | Root | 1DAR | 51.08 ± 17.34 |
| V7 | Root | Ctrl | 60.67 ± 19.04 |
| V7 | Root | Des1 | 22.36 ± 17.87 |
| V7 | Root | Des2 | 40.04 ± 7.20 |
| V7 | Root | 1DAR | 55.60 ± 15.92 |
| VT | Root | Ctrl | 44.07 ± 0.00 |
| VT | Root | Des1 | 75.82 ± 20.65 |
| VT | Root | Des2 | 37.09 ± 7.55 |
| VT | Root | 1DAR | 2.43 ± 0.31 |
| 3 DAG | Coleoptile | Ctrl | 138.38 ± 25.13 |
| 3 DAG | Coleoptile | Cold | 127.45 ± 30.79 |
| V3 | Leaf | Ctrl | 22.51 ± 8.74 |

TABLE 2-continued

Zm.NFB2 Regulatory Element Expression in Transgenic Corn Plant Tissues

| Stages | Organ | Inducer | Mean ± SE |
|---|---|---|---|
| V3 | Leaf | Cold | 36.77 ± 14.43 |
| V3 | Leaf | Des1 | 28.11 ± 14.38 |
| V3 | Leaf | Des2 | 24.55 ± 4.31 |
| V3 | Leaf | 1DAR | 19.94 ± 17.31 |
| V7 | Leaf - Mature | Ctrl | 56.61 ± 18.71 |
| V7 | Leaf - Mature | Des1 | 22.66 ± 8.75 |
| V7 | Leaf - Mature | Des2 | 48.55 ± 14.98 |
| V7 | Leaf - Mature | 1DAR | 91.14 ± 28.63 |
| VT | Leaf - Mature | Ctrl | 66.59 ± 36.97 |
| VT | Leaf - Senescence | Sens. | 34.32 ± 17.20 |
| VT | Leaf - Mature | Des1 | 48.07 ± 17.13 |
| VT | Leaf - Mature | Des2 | 36.06 ± 15.16 |
| VT | Leaf - Mature | 1DAR | 22.85 ± 12.12 |
| VT | Cob | Ctrl | 150.17 ± 23.41 |
| VT | Cob | Des1 | 114.89 ± 29.41 |
| VT | Cob | Des2 | 161.86 ± 29.36 |
| VT | cob | 1DAR | 148.16 ± 28.36 |
| VT | Silk | Ctrl | 28.71 ± 5.56 |
| VT | Silk | Des1 | 47.92 ± 10.61 |
| VT | Silk | Des2 | 38.45 ± 6.40 |
| VT | Silk | 1DAR | 34.25 ± 4.28 |
| VT | Internode | — | 1.04 ± 0.00 |
| VT | Anther | — | 65.44 ± 13.08 |
| VT | Pollen | — | 13.21 ± 3.20 |
| 21 DAP | Embryo | — | 119.30 ± 12.01 |
| 35 DAP | Embryo | — | 30.35 ± 3.48 |
| 7 DAP | Kernel | — | 74.35 ± 5.89 |
| 21 DAP | Endosperm | — | 57.65 ± 4.97 |
| 35 DAP | Endosperm | — | 13.07 ± 2.50 |

TABLE 3

Zm.NFB2 Regulatory Element Expression in Transgenic Corn Cell Types
Table 2 Qualitative GUS expression analysis

| Stage | Inducers | Tissue | Cell types | | | |
|---|---|---|---|---|---|---|
| Imbibed seed | — | Seed | ⊔pericarp ⊡embryo | ⊠endosperm | ⊡scutellum | ⊔nd |
| 3 DAG | — | Root | ⊞epidermis ⊞stele | ⊞cortex ⊡root hair | ⊞endoderm ⊡root tip | ⊔nd ⊠root WM |
| V3 | — | Root | ⊞epidermis ⊞stele | ⊞cortex ⊡root hair | ⊞endoderm ⊡root tip | ⊔nd ⊡root WM |
| V3 | Cold | Root | ⊞epidermis ⊞stele | ⊞cortex ⊠root hair | ⊞endoderm ⊠root WM | ⊔nd ⊡root tip |
| V3 | Desiccation | Root | ⊞epidermis ⊞stele | ⊞cortex ⊞root hair | ⊞endoderm ⊠root WM | ⊔nd ⊠root tip |
| V7 | — | Root | ⊞epidermis ⊞stele | ⊞cortex ⊡root hair | ⊞endoderm ⊡root WM | ⊔nd ⊡root tip |
| VT | — | Root | ⊞epidermis ⊞stele | ⊞cortex ⊡root hair | ⊞endoderm ⊠root WM | ⊔nd ⊠root tip |
| 3 DAG | — | Apical regions | ⊡shoot apex | ⊡coleoptiles | | ⊔nd |
| V3 | — | Leaf | ⊡epidermis ⊡bundle sheath | ⊡guard cells ⊠vascular bundle | ⊡mesophyll | ⊔nd |
| V3 | Cold | Leaf | ⊡epidermis ⊡vascular bundle | ⊡mesophyll ⊡guard cell | ⊠bundle sheath | ⊔nd |
| V3 | Desiccation | Leaf | ⊠epidermis ⊡vascular bundle | ⊡mesophyll ⊞guard cell | ⊡bundle sheath | ⊔nd |
| V7 | — | Leaf - (source) | ⊡epidermis ⊠vascular bundle | ⊡mesophyll ⊡guard cell | ⊡bundle sheath | ⊔nd |
| VT | — | Leaf - (source) | ⊡epidermis ⊡vascular bundle | ⊠mesophyll ⊠guard cell | ⊠bundle sheath | ⊔nd |
| V7 | — | Node | ⊔vascular bundle | ⊔parenchyma | | ⊞nd |
| VT | — | Node | ⊠vascular bundle | ⊠parenchyma | | ⊔nd |
| V7 | — | Internode - elongating | ⊔vascular bundle | ⊔parenchyma | | ⊞nd |
| VT | — | Internode - elongated | ⊡vascular bundle | ⊠parenchyma | | ⊔nd |
| V7 | — | Tassel primordia | ⊡rachis primordia | ⊠floret primordia | | ⊔nd |
| VT | — | spikelet | ⊠rachis ⊡filament | ⊠glume ⊡anther | ⊠lemma & palea ⊡pollen grains | ⊔nd |
| V7 | — | Cob primordia | ⊡cob primordia | | | ⊔nd |

TABLE 3-continued

Zm.NFB2 Regulatory Element Expression in Transgenic Corn Cell Types
Table 2 Qualitative GUS expression analysis

| Stage | Inducers | Tissue | Cell types | | | | |
|---|---|---|---|---|---|---|---|
| VT | — | Cob | ☒ cob vasculature<br>☒ glume/palea | ☒ pedicel<br>☒ carpel | ☒ silk | | ⌐ nd |
| 7 DAP | — | Kernel | ⌐ pericarp | ⌐ pedicel | ⌐ endosperm | ⌐ embryo | ■ nd |
| 10 DAP | — | Kernel | ☒ pericarp<br>☒ embryo | ☒ pedicel<br>■ scutellum | ☒ endosperm<br>■ aleurone | | ⌐ nd |
| 14 DAP | — | Kernel | ⌐ pericarp<br>⌐ embryo | ⌐ pedicel<br>⌐ scutellum | ⌐ endosperm<br>⌐ aleurone | | ■ nd |
| 21 DAP | — | Kernel | ☒ pericarp<br>☒ embryo | ☒ pedicel<br>☒ scutellum | ☒ endosperm<br>■ aleurone | | ⌐ nd |
| 28 DAP | — | Kernel | ⌐ pericarp<br>⌐ embryo | ⌐ pedicel<br>⌐ scutellum | ⌐ endosperm<br>⌐ aleurone | | ■ nd |
| 35 DAP | — | Kernel | ☒ pericarp<br>☒ embryo | ☒ pedicel<br>☒ scutellum | ☒ endosperm<br>■ aleurone | | ⌐ nd |

■☒ GUS expression detected
⌐ No GUS Expression Detected
■ Not determined

Histochemical assay and MUG assay showed expression at all the developmental stages in all the tissues tested. GUS staining has shown intense blue colour in young tissues like cob primordia, tassel primordia and shoot apex. The Zm.NFB2 expression elements have thus been shown to be useful in expressing transgenes in a constitutive manner.

The present invention thus provides DNA constructs comprising regulatory elements that can modulate expression of an operably linked transcribable polynucleotide molecule and a transgenic plant stably transformed with the DNA construct. From the examples given, the present invention thus provides isolated regulatory elements and isolated promoter fragments from *Oryza sativa*, that are useful for modulating the expression of an operably linked transcribable polynucleotide molecule. The present invention also provides a method for assembling DNA constructs comprising the isolated regulatory elements and isolated promoter fragments, and for creating a transgenic plant stably transformed with the DNA construct.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. A polynucleotide molecule comprising a nucleic acid sequence selected from the group consisting of:
    (a) the nucleic acid sequence of SEQ ID NO:1 or SEQ ID NO:2; and
    (b) a fragment of at least 50 contiguous bases of SEQ ID NO:1 or SEQ ID NO:2 wherein said fragment comprises promoter activity, and wherein the polynucleotide molecule is operably linked to a heterologous transcribable polynucleotide molecule.

2. The polynucleotide molecule of claim 1, wherein said transcribable polynucleotide molecule comprises a coding sequence of agronomic interest.

3. The polynucleotide molecule of claim 1, wherein said transcribable polynucleotide molecule comprises a coding sequence controlling the phenotype of a trait selected from the group consisting of: herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

4. The polynucleotide molecule of claim 3, wherein said herbicide tolerance coding sequence is selected from the group consisting of coding sequences for: phosphinothricin acetyltransferase, glyphosate resistant EPSPS, hydroxyphenyl pyruvate dehydrogenase, dalapon dehalogenase, bromoxynil resistant nitrilase, anthranilate synthase, glyphosate oxidoreductase and glyphosate-N-acetyl transferase.

5. A transgenic plant cell stably transformed with the polynucleotide molecule of claim 1.

6. A transgenic plant stably transformed with the polynucleotide molecule of claim 1.

7. A seed of said transgenic plant of claim 6, wherein the seed comprises the polynucleotide molecule.

8. A progeny of the plant of claim 6, wherein the progeny comprises the polynucleotide molecule.

9. The transgenic plant cell of claim 5, wherein said plant cell is from a monocotyledonous plant selected from the group consisting of wheat, maize, rye, rice, corn, oat, barley, turfgrass, sorghum, millet and sugarcane.

10. The transgenic plant of claim 6, wherein said plant is a monocotyledonous plant selected from the group consisting of wheat, maize, rye, rice, corn, oat, barley, turfgrass, sorghum, millet and sugarcane.

11. A seed of the transgenic plant of claim 10, wherein the seed comprises the polynucleotide molecule.

12. A transgenic plant cell of claim 5, wherein said plant cell is from a dicotyledonous plant selected from the group consisting of tobacco, tomato, potato, soybean, cotton, canola, sunflower and alfalfa.

13. The transgenic plant of claim 6, wherein said plant is a dicotyledonous plant selected from the group consisting of tobacco, tomato, potato, soybean, cotton, canola, sunflower and alfalfa.

14. A seed of the transgenic plant of claim 13, wherein the seed comprises the polynucleotide molecule.

15. A method of inhibiting weed growth in a field of transgenic glyphosate-tolerant crop plants comprising: planting transgenic plants transformed with an expression cassette comprising the polynucleotide molecule of claim 1 wherein the transcribable polynucleotide molecule confers glyphosate tolerance to said transgenic plants; and applying glyphosate to the field at an application rate that inhibits the growth of weeds.

* * * * *

UNITED STATES PATENT AND TRADEMARK OFFICE
CERTIFICATE OF CORRECTION

PATENT NO. : 8,772,466 B2  
APPLICATION NO. : 12/331214  
DATED : July 8, 2014  
INVENTOR(S) : Donald E. Nelson et al.

Page 1 of 1

It is certified that error appears in the above-identified patent and that said Letters Patent is hereby corrected as shown below:

IN THE CLAIMS:

Column 41, Line 15, please delete "orSEQ ID NO:2" and insert --or SEQ ID NO:2--

Signed and Sealed this  
Twentieth Day of January, 2015

Michelle K. Lee  
*Deputy Director of the United States Patent and Trademark Office*

SEQUENCE LISTING

<160> NUMBER OF SEQ ID NOS: 5

<210> SEQ ID NO 1
<211> LENGTH: 1031
<212> TYPE: DNA
<213> ORGANISM: Zea mays

<400> SEQUENCE: 1

```
gatcgtgatt taaccgcaag tcacatttag cacttaaatc cttccaccac cagctcaata      60
atctttataa aaaacccct aacaaatcat ggttgtatct gtggttggat cgtaatctaa     120
tgaatcaaat agtttgcttg cacgcttaca cagaaacact gcttgcatag cagtcgttgc     180
ctatgtctta catgcaaatt tcatgagtca tgggctcata accaatgcca ctggtacact     240
gttataagga atattcgtcc tagcgtaaag aacttaagta tattaatata atttaccta     300 cacatctaaa gaagcacaaa tccattgaaa atgataaatt tcagttctta ccttgtcctc     360
gatctcatct gttttgattg ctggtaaata cattcgatcc tttttttaaa aaaaaactga     420
agatattttt gccacttcaa tctatttga cgtgatcata cggaccgcca ggcatttttt     480
ttcgcctttc tttaacctca tctcatcggc aattaaagac cagggaaata gtaattgcga     540
caggcttctc tggtcctatt ggcgatcagg acaacccacc taaaacacat gccaaaaagg     600
gctttctctc cctgctgaac accaactacc ctgcgccggg tccagggtgc gccgggttct     660
ccctctcgct cccacgcggc aaaccccacg acgtgctata atattccac gaacggcccg     720
```

```
gatacctcca gccccgcatc gcaccctccc tggccgcctt ctcttctcca gcgtccgatc    780
tctcccactc gccttcctca ccgcagctct cccggctcgg tcgcttcgcc acctccgtcc    840 tcccccgcg ctcggtcgct cgccacctgc tctcccctcc ctccacgttg ctcgcgcccg     900
cgcttatata aggtacgccg cctcgactct ccaaacccct ccgcgtggac ctaaggtccg    960
gcgcgccgag atggagctga tggatctagg gtttcggttg cggcggcggt cctgtagtgc   1020
aggaggagct c                                                        1031

<210> SEQ ID NO 2
<211> LENGTH: 728
<212> TYPE: DNA
<213> ORGANISM: Zea mays

<400> SEQUENCE: 2
gatcgtgatt taaccgcaag tcacatttag cacttaaatc cttccaccac cagctcaata     60
atctttataa aaaacccct aacaaatcat ggttgtatct gtggttggat cgtaatctaa    120
tgaatcaaat agtttgcttg cacgcttaca cagaaacact gcttgcatag cagtcgttgc    180
ctatgtctta catgcaaatt tcatgagtca tgggctcata accaatgcca ctggtacact    240
gttataagga atattcgtcc tagcgtaaag aacttaagta tattaatata atttacctta    300
cacatctaaa gaagcacaaa tccattgaaa atgataaatt tcagttctta ccttgtcctc    360
gatctcatct gttttgattg ctggtaaata cattcgatcc ttttttaaa aaaaaactga    420 agatatttt gccacttcaa tctatttga cgtgatcata cggaccgcca ggcattttt     480 ttcgcctttc tttaacctca tctcatcggc aattaaagac cagggaaata gtaattgcga    540
caggcttctc tggtcctatt ggcgatcagg acaacccacc taaaacacat gccaaaaagg    600
gctttctctc cctgctgaac accaactacc ctgcgccggg tccagggtgc gccgggttct    660
ccctctcgct cccacgcggc aaaccccacg acgtgctata atattccac gaacggcccg    720 gatacctc                                                            728

<210> SEQ ID NO 3
<211> LENGTH: 184
<212> TYPE: DNA
<213> ORGANISM: Zea mays

<400> SEQUENCE: 3
cagccccgca tcgcaccctc cctggccgcc ttctcttctc cagcgtccga tctctcccac     60
tcgccttcct caccgcagct ctcccggctc ggtcgcttcg ccacctccgt cctcccccg    120 cgctcggtcg ctcgccacct gctctcccct ccctccacgt tgctcgcgcc cgcgcttata    180
taag                                                                184

<210> SEQ ID NO 4
<211> LENGTH: 105
<212> TYPE: DNA
<213> ORGANISM: Zea mays

<400> SEQUENCE: 4
gtacgccgcc tcgactctcc aaacccctcc gcgtggacct aaggtccggc gcgccgagat     60
ggagctgatg gatctagggt ttcggttgcg gcggcggtcc tgtag                   105

<210> SEQ ID NO 5
<211> LENGTH: 14
<212> TYPE: DNA
```

```
<213> ORGANISM: Zea mays

<400> SEQUENCE: 5
tgcaggagga gctc                                                        14
```